(12) United States Patent
Galley et al.

(10) Patent No.: US 8,515,775 B2
(45) Date of Patent: Aug. 20, 2013

(54) HANDHELD DIABETES MANAGEMENT DEVICE FOR OBTAINING THREE DAY BLOOD GLUCOSE PROFILE

(75) Inventors: Paul J. Galley, Cumberland, IN (US); John F. Price, McCordsville, IN (US); Richard W. Wilson, Fortville, IN (US); Lisa McCool, Newburgh, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 336 days.

(21) Appl. No.: 12/905,417

(22) Filed: Oct. 15, 2010

(65) Prior Publication Data

US 2012/0095773 A1 Apr. 19, 2012

(51) Int. Cl.
*G06Q 50/00* (2006.01)

(52) U.S. Cl.
USPC .......................................................... 705/2

(58) Field of Classification Search
USPC .......................................................... 705/2, 3
See application file for complete search history.

(56) References Cited

U.S. PATENT DOCUMENTS

| | | | |
|---|---|---|---|
| 7,291,107 B2 | 11/2007 | Hellwig et al. | |
| 7,553,281 B2 | 6/2009 | Hellwig et al. | |
| 2001/0045355 A1* | 11/2001 | Gephart et al. | 204/400 |
| 2004/0059201 A1* | 3/2004 | Ginsberg | 600/300 |
| 2004/0172284 A1 | 9/2004 | Sullivan et al. | |
| 2006/0047192 A1 | 3/2006 | Hellwig et al. | |
| 2006/0137695 A1 | 6/2006 | Hellwig et al. | |
| 2008/0058628 A1 | 3/2008 | Hellwig et al. | |
| 2009/0177147 A1* | 7/2009 | Blomquist et al. | 604/67 |
| 2010/0069730 A1 | 3/2010 | Bergstrom et al. | |
| 2010/0160757 A1 | 6/2010 | Weinert et al. | |
| 2010/0160759 A1 | 6/2010 | Celentano et al. | |
| 2010/0168660 A1 | 7/2010 | Galley et al. | |
| 2010/0212675 A1 | 8/2010 | Walling et al. | |
| 2010/0218132 A1 | 8/2010 | Soni et al. | |
| 2010/0331650 A1 | 12/2010 | Batman | |
| 2011/0152657 A1* | 6/2011 | Bielawa et al. | 600/365 |
| 2011/0208027 A1* | 8/2011 | Wagner et al. | 600/365 |

OTHER PUBLICATIONS

Smiths Medical MD, Inc., Deltec Cozmo®, Fine Tuning Your Deltec Cozmo® Insulin Pump Settings, Overnight Basal Rate Test Instructions, 2 pp, Apr. 2007.
Smiths Medical MD, Inc., Deltec Cozmo®, User Manual, Deltec Cozmo® Insulin Pump, 245 pp, 2006.

* cited by examiner

*Primary Examiner* — Gerald J. O'Connor
*Assistant Examiner* — Trang Nguyen
(74) *Attorney, Agent, or Firm* — Harness, Dickey

(57) ABSTRACT

A method is disclosed for managing a three day profile blood glucose (bG) measurements that are provided by a user using a handheld diabetes management device. The method may involve configuring a database carried by the device to store a plurality of bG test values input by a user for each day of a three day test period. The bG test values are required to be provided by the user in accordance with a predetermined plurality of differing acceptance time windows during each day of the three day test period. If two or more windows are open concurrently when a given bG test value is obtained, the system allows the user to select the appropriate time window that the given bG test value should be associated with. A processing subsystem of the device determines if at least a predetermined minimum plurality of the stored bG test values has been provided by the user during the predetermined plurality of differing acceptance time windows for each day of the three day test period and, if so, the processing subsystem accepts the bG test values provided by the user when compiling results for a three day bG profile.

18 Claims, 5 Drawing Sheets

HANDHELD DIABETES MANAGEMENT DEVICE FOR OBTAINING THREE DAY BLOOD GLUCOSE PROFILE

FIELD

This disclosure relates to diabetes care medical devices used for diagnostics and therapy, and more particularly to a handheld diabetes management device that incorporates a three day blood glucose profile that can be run in an automated fashion on the device to automatically provide acceptance time windows at user-configured times and to record blood glucose test values that can be displayed to the user in a tabular or graphical format.

BACKGROUND

The statements in this section merely provide background information related to the present disclosure and may not constitute prior art.

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. Its incidence is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Management of diabetes is complex as the level of blood glucose entering the bloodstream is dynamic. Variation of insulin that controls the transport of glucose out of the bloodstream also complicates diabetes management. Blood glucose levels are sensitive to diet and exercise, but also can be affected by sleep, stress, smoking, travel, illness, menses, and other psychological and lifestyle factors unique to individual patients. The dynamic nature of blood glucose and insulin, and all other factors affecting blood glucose, often require a person with diabetes to understand ongoing patterns and forecast blood glucose levels (or at least understand the actions that raise or lower glucose in the body). Therefore, therapy in the form of insulin or oral medications, or both, can be timed to maintain blood glucose levels in an appropriate range.

Management of diabetes is often highly intrusive because of the need to consistently obtain reliable diagnostic information, follow prescribed therapy, and manage lifestyle on a daily basis. Daily diagnostic information, such as blood glucose, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an insulin pen, an ambulatory infusion pump, or a combination of such devices. With insulin therapy, determining the amount of insulin to be injected can require forecasting meal composition of carbohydrates, fat and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data that are acquired from medical devices, personal healthcare devices, patient recorded information, healthcare professional tests results, prescribed medications and recorded information. Medical devices including self-monitoring bG meters, continuous glucose monitors, ambulatory insulin infusion pumps, diabetes analysis software, and diabetes device configuration software each of which generates or manages or both large amounts of diagnostic and prescriptive data. Personal healthcare devices include weight scales, pedometers and blood pressure cuffs. Patient recorded information includes information relating to meals, exercise and lifestyle as well as prescription and non-prescription medications. Healthcare professional biomarker data includes HbA1C, cholesterol, triglycerides, and glucose tolerance. Healthcare professional recorded information includes therapy and other information relating to the patient's treatment.

There is a need for a handheld patient device to aggregate, manipulate, manage, present, and communicate diagnostic data and prescriptive data from medical devices, personal healthcare devices, patient recorded information, biomarker information and recorded information in an efficient manner to improve the care and health of a person with diabetes, so the person with diabetes can lead a full life and reduce the risk of complications from diabetes.

It will also be appreciated that at the present time, patients with diabetes may be asked to periodically assess their daily glycemic control, for example by conducting a three day blood glucose (bG) test. This involves the patient checking his/her bG several times during consecutive twenty four hour periods and manually recording the data in a chart. Preferably, the three day bG test is done with the patient checking his/her bG levels at seven different times during the day: 1) pre-breakfast; 2) post-breakfast; 3) pre-lunch; 4) post-lunch; 5) pre-dinner; 6) post-dinner; and 7) bedtime. The results of each of the bG tests may be recorded manually by the patient. The bG tests need to be performed within the context for each of the above-described seven events (which may include a predetermined time window). As will be appreciated, this can be somewhat of a burdensome procedure for the patient. It is also important that the patient record all of the obtained bG information correctly on the three-day bG test chart. The information must be accurately and legibly recorded on the chart, typically using a writing implement such as a pencil or pen. Thus, while carrying out the three day bG profile the user is typically required to carry a pencil or pen with him or her as well as the bG testing supplies, which as will be appreciated may cause a degree of inconvenience to the user. Typically the user must carry, in a purse or pocket, the paper chart for recording the bG test values, which may also add some inconvenience to the user. Finally, it is important that the user not misplace or otherwise damage the paper chart while carrying out the test, lest important bG test information becomes unavailable or unreadable, thus requiring the test to be started over. Automating the three day bG profile through a handheld device that can be carried more easily on the person of a user would significantly reduce the possibility of a paper chart being lost, misplaced or otherwise damaged to the point where the data recorded thereon is unreadable.

SUMMARY

This section provides a general summary of the disclosure, and is not a comprehensive disclosure of its full scope or all of its features.

In one aspect the present disclosure relates to a method for managing three day profile blood glucose (bG) measurements provided by a user on a handheld diabetes management device. The method can comprise configuring a database of the device to store a plurality of bG test values input by a user for each day of a three day test period, wherein bG test values are required to be provided by the user in accordance with a predetermined plurality of differing acceptance time windows during each day of the three day test period. A processing subsystem of the device can be used to receive bG test values provided by the user and to store the bG test values in the database of the device. The method allows two or more acceptance time windows to be opened at the same time, and if a given bG test value is obtained during such a condition, then the user is allowed to select which one of the open acceptance time windows to associate the given bG test value with. The processing subsystem can be used to determine if at least a predetermined minimum plurality of the stored bG test values has been provided by the user during the predetermined plurality of differing acceptance time windows for each day of the three day test period. If so, the processing subsystem can accept the bG test values for the purpose of compiling results for a three day bG profile.

In another aspect the present disclosure relates to a non-transitory, computer readable medium. The computer readable medium is adapted to run on a processing subsystem of a handheld diabetes device for managing three day profile blood glucose (bG) measurements input by a user to the device. The computer readable medium can comprise a database that stores a plurality of bG test values input to the device by a user for each day of a three day test period. The bG test values can be provided by the user in accordance with a predetermined plurality of differing acceptance time windows during each day of the three day test period. The computer readable medium is adapted to determine if at least a predetermined minimum plurality of the stored bG test values has been accepted during the predetermined plurality of differing acceptance time windows for each day of the three day test period. If so, the accepted bG test values are used as test results for a three day bG profile. The computer readable medium is also able to determine if the first two days of the three day test period each have the minimum plurality of the stored bG test values obtained therefore, and that the third day does not, and then enables the test to continue on a successive fourth day following the third day in an attempt to successfully complete the three day test period.

In another aspect the present disclosure relates to a system for managing three day profile blood glucose (bG) measurements provided by a user. The system can comprise a handheld diabetes management device. The device can include a database for storing bG values input to the device by a user for each day of a three day test period. The device can also include a processing subsystem in communication with the database. The processing system can be configured to perform several operations: to generate a plurality of acceptance time windows for a twenty four hour period; to analyze the bG test values stored in the database during each twenty four hour period for each day over a three day period; to determine whether each of the stored bG test values corresponds to a meal; to accept only the bG test values input by the user that correspond to a meal, and that have been input during specific ones of the plurality of acceptance time windows over the three day period; and to use the accepted bG values in generating information relating to test results for a three day bG profile. The system can also determine if a sufficient number of accepted bG test values has been obtained for each of the first and second days of the three day test, but the third day of the test did not, then allowing the user to attempt to complete the test by entering bG test values on a fourth day following the third day of the test. The handheld diabetes management device may further include a display that displays the results of the three day bG profile.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The following figures are selected embodiments of the handheld diabetes manager with enhanced data capacity and related system embodiments and information.

DETAILED DESCRIPTION

Figure 1:
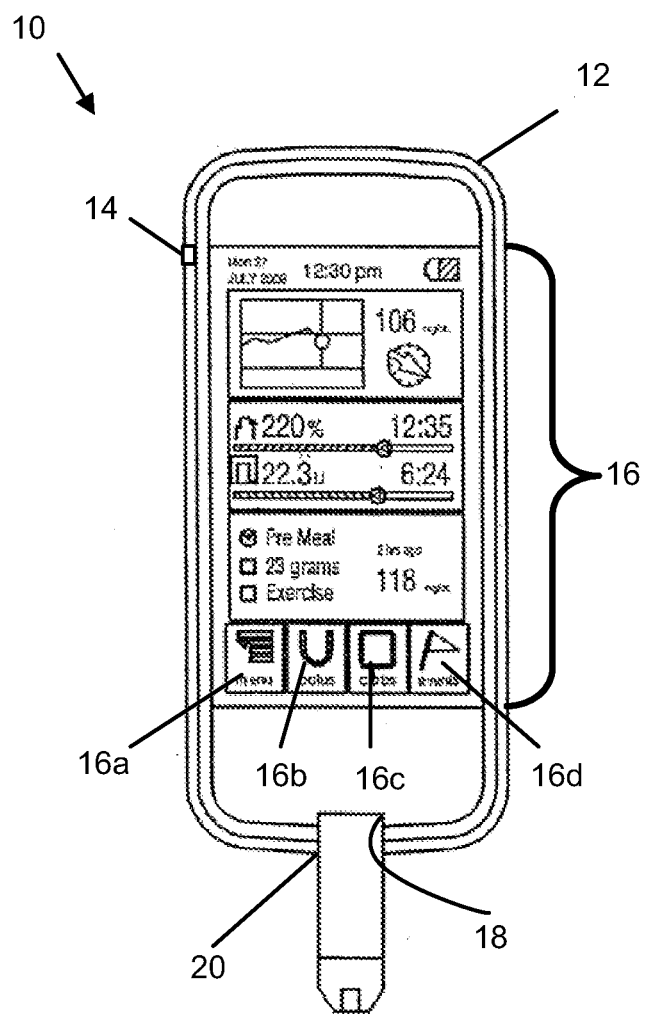
FIG. 1 is a perspective view of one embodiment of a handheld diabetes bG management device in accordance with the present disclosure.

The following description is merely exemplary in nature and is not intended to limit the present disclosure, application, or uses. It should be understood that throughout the drawings, corresponding reference numerals indicate like or corresponding parts and features.

Referring to FIG. 1, there is shown a high level drawing of one embodiment of a handheld, portable blood glucose (bG) monitoring device 10 that may be used by a user in obtaining a three day bG profile. The device 10 can include a housing 12 that may contain one or more user actuatable unit control switches 14 (e.g., ON/OFF), a color (or black and white) touchscreen display 16, and a port 18 into which a bG test strip 20 may be inserted. The display 16 may display user selectable options for allowing the user to access a software driven menu 16a of a software module stored in the device 10 so that the user can make various selections while initiating, carrying out or concluding the 3 day bG profile. A menu selection 16b allows the user to enter bolus information, while a selection 16c enables the user to enter carbohydrate information for snacks or meals. A selection 16d allows the user to enter information pertaining to events (e.g., meals, exercise, periods of stress, etc.) that may affect the user's bG measurement being read by the device 10. Although the display 16 will be described herein as a color touchscreen display, it will be appreciated that any other suitable form of display may be incorporated (e.g., LED, LCD, etc.). If a touchscreen display is not used, the user control switches 14 may need to include specific buttons or controls by which the user is able to select various options and input markers needed to carry out the three day bG profile test. It will be appreciated that the above is a high level description of the device 10, and in practice the device may include additional controls, input ports, output ports, etc., as may be desired to even further enhance the utility of the device 10 or its use with other components and devices (e.g., laptop computers, infusion pumps, etc.). Accordingly, the above description of the device 10 should not be taken as limiting its construction or features in any way.

Figure 2:
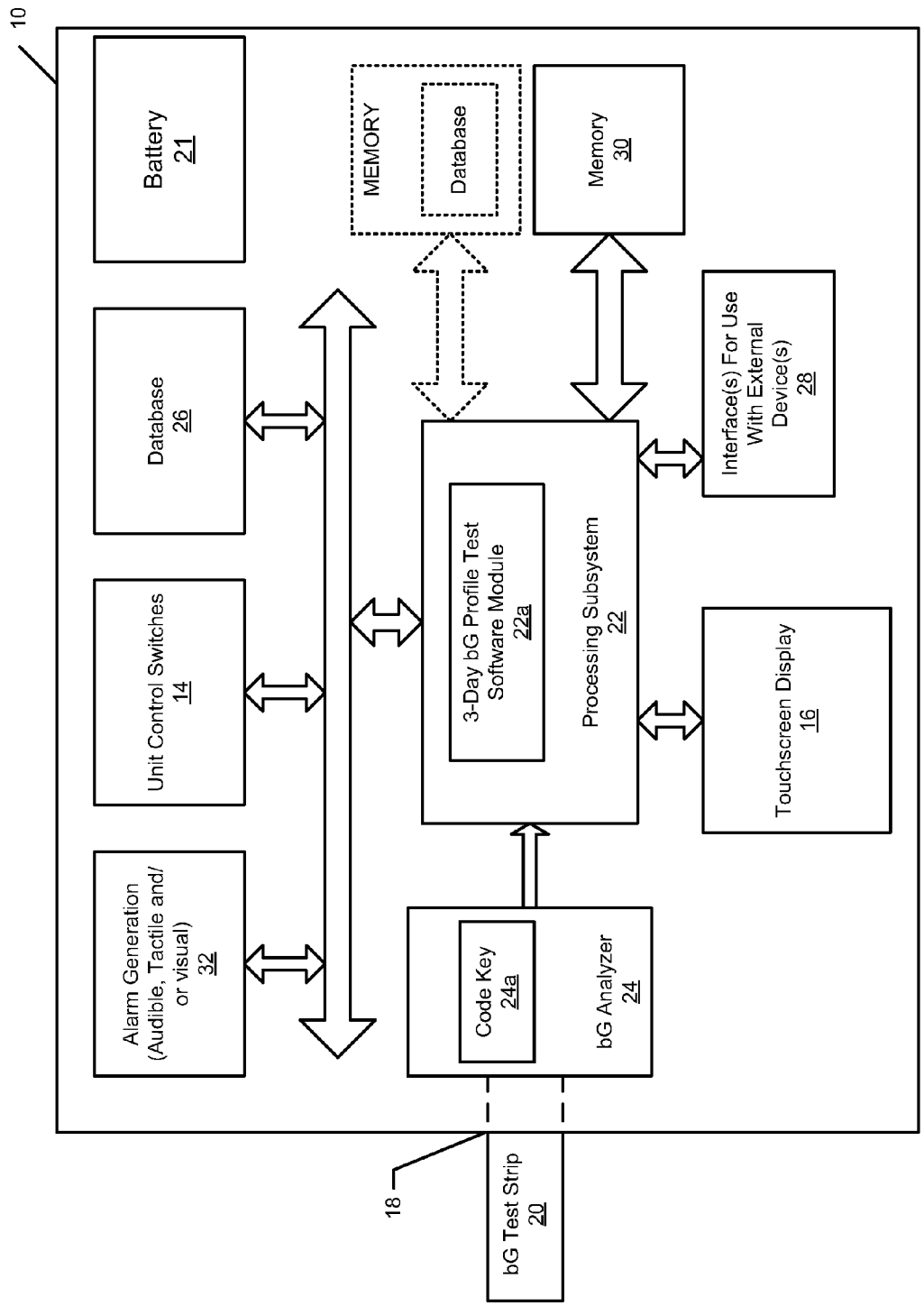
FIG. 2 is a high level block diagram of various components and subsystems that may be incorporated in the device shown in FIG. 1.

Referring to FIG. 2, a high level block diagram of the device 10 is shown. The device 10 may include a suitable rechargeable battery 21 for powering all the electronic components of the device 10. A processing subsystem 22 (e.g., a microprocessor based subsystem) receives information from a bG analyzer 24. The bG analyzer 24 is located adjacent the port 18 of the housing 12 to permit the bG analyzer 24 to read the bG test strip 20. The bG analyzer 24a may include a code key 24a that includes calibration for the bG test strip 20 being read. The processing subsystem 22 may also be in communication with a database 26, which may form a relational database, which is used to store bG test values obtained from the bG analyzer 24. The processing subsystem 22 may also be in contact with the display 16, the user control panel 14, and one or interfaces 28 for interfacing the device 10 to other external devices. The processing subsystem 22 may also be in communication with a memory 30 for storing various types of information (e.g., meal times) that are input by the user, as well as any other information requiring temporary or permanent storage. However, it will be appreciated that the database 26 and the memory 30 could be implemented in a single memory device (e.g., RAM) if desired, as indicated in phantom in FIG. 2. Finally the processing subsystem 22 may be in communication with an alarm generation subsystem 32 that may be used to generate an alarm consisting of audible signals, tactile signals (e.g., a vibration signal) or even possibly visual signals such as illuminated lights (e.g., LEDs) on the device 10.

The device 10 may be used to implement a non-transitory machine readable code, for example a software module 22a, that is run by the processing subsystem 22. The processing subsystem 22, working in connection with the software module 22a, initiates and controls the operation of a three day bG profile test, and may present the collected bG test value data obtained during the test in various forms on the display 16. The device 10 significantly enhances the convenience and ease to the user in carrying out a three day bG profile test, which hereinbefore has been required to be performed by the user by manually recording bG test information before and after meals on a paper chart with a suitable writing implement, such as a pen or pencil. By using the device 10, the three day bG profile may be automated to eliminate the need for the user to use a paper chart to manually record the bG test data. Automating the operations required to construct a three day bG profile also enables a significant number of highly desirable features to be implemented, such as reminding the user at the appropriate times of the day of the need to obtain and enter bG test information, as well as to organize and segregate the bG test results so that only those bG tests that are obtained at predetermined times throughout a three day window, and marked accordingly by the user, are used in compiling and presenting the results of the test. The device 10 may reduce the likelihood that a user forgets to obtain a bG reading at a required time or does not obtain a required number of bG test values in a given day to enable successful completion of a valid three day bG profile test.

To set up a three day bG profile test the user may select this option by navigating through various menu items that are displayed and selected through the "Menu" control 16a on touchscreen display 16. The user may select a typical breakfast time, a typical lunch time, a typical dinner time, and a typical bed time, and input these times into the device 10 via the touchscreen display 16. These times may be stored in the memory 30 or alternatively in the database 26. The user may also input a snack "threshold" (e.g., carbohydrate threshold) using the touchscreen display 16, which is also stored in the memory 30 (or possibly the database 26), to distinguish snacks from meals. A bG test result that accompanies a carbohydrate entry that is below the set snack threshold is marked and stored by the processing subsystem 22 as a "snack" rather than as a "meal". A carbohydrate entry above the set snack threshold may be marked by the device 10 as a meal. The touchscreen display 16 may also be used to allow the user to enter bG markers that designate whether an obtained bG test value is preprandial (i.e., pre-meal), postprandial (i.e., post-meal), or bedtime.

The software module 22a provides predetermined "acceptance" time windows of varying lengths during which bG test values must be entered by the user for the bG values to be included in the three day bG profile. In one embodiment the software module 22a implements acceptance time windows for user provided preprandial bG test values within two hours of the user typical breakfast, lunch and dinner meal times. The bedtime acceptance time window may be set to within two hours of the user typical bedtime. The postprandial acceptance time windows may be set to begin ninety minutes after each of the actual breakfast, lunch and dinner times. While the above described acceptance time windows may be varied through programming modifications to the software module 22a, it is preferred that the user not be able to directly edit or alter the preprandial, bedtime and postprandial acceptance time windows during the course of an active three day profile test. Maintaining these predetermined acceptance time windows at the above described durations helps to ensure consistency for pattern recognition Identification, especially of postprandial excursions, should demonstrate lower glucose variability when the relative measurement time (e.g., 90 to 150 min) is enforced. Likewise, long-acting insulin is expected to be delivered at about the same time every day. Helping to support a more uniform basal insulin dosing time should reduce fasting blood glucose variability.

When the user inserts a bG test trip into the port 18 of the device 10, the bG analyzer 24 reads the test strip and provides a bG test value and an associated time stamp to the processing subsystem 22 that identifies precisely when the bG test value was obtained. If only a single acceptance time window is open at this time, and the acceptance window is one relating to a preprandial, postprandial, or bedtime acceptance time window, then the bG test value qualifies for inclusion in the three day bG profile test and may be automatically stored in the database 26 by the processing subsystem 22. If more than one acceptance time window is open at this time, the processing subsystem 22 will provide a query on the display 16 asking the user to specify the label for the bG value. The display 16 may show selection boxes for the specific preprandial, postprandial, or bedtime event that the user may select simply by touching the appropriate selection on the display 16. This is a significant feature of the device 10 as it automatically detects the occurrence of two or more overlapping acceptance time windows and automatically provides the required message to the user to positively identify which type of event that the just-obtained bG test value is associated with. It will also be appreciated that it is a significant advantage of the device 10 that the user is able to select among overlapping time windows. This provides significant flexibility to the user in the event that the user has one or more meal times that may occasionally overlap. For example, if the user has a job that requires traveling between multiple locations and meetings before or after lunch, there may be times when the user needs to take an early lunch or a late lunch. Allowing the user to configure the device so that two acceptance windows (e.g., post-breakfast and pre-lunch) overlap slightly permits the user to accommodate those situations where the user needs to take an early or late meal because of her/his work schedule. Importantly, since the device 10 is able to recognize this situation, the user will automatically be alerted when two overlapping acceptance time windows happen to be open simultaneously, and the user provided with an opportunity to label a specific bG test value in accordance with its proper event.

Another important feature of the device 10 is that if the user obtains a bG test value outside of one of the predefined acceptance time windows (i.e., while no acceptance time window is open) or the user chooses to associate no label, then the device 10 will store the bG test value in the database 26 but will not include it in the three day bG profile results file(s). Thus, this bG test value will still be available to the user or a clinician in evaluating the user's bG history. But importantly the device 10 prevents the bG test value from being used to form a portion of the three day bG profile.

To assist the user in carrying out the three day bG profile, the device 10 may be configured by the user to provide reminders to carry out a bG test for each acceptance time window. The user can optionally be provided with the option to select one of at least three responses to a just-given reminder: "Accept"; "Dismiss"; and "Snooze". It will be understood that the "Accept" and "Dismiss" options could be replaced by a single "OK" or "Close" option with subsequent behavior dependent on the successful completion of a bG test within an acceptance window. In any event, these optional selections may be provided on the display 16 with a check box that the user may select via a touch selection. An "Accept" selection may indicate to the device 10 the user's acknowledgement of the reminder and that the user intends to enter a bG test value within a predetermined number of minutes (e.g., within five minutes). The "Dismiss" selection may allow the user to immediately dismiss the reminder, and all potential follow up reminders, for that particular acceptance time window. The user selecting the "Snooze" option in response to a generated reminder may signal to the processing subsystem 22 to repeat the reminder if the user does not respond to the reminder. The reminder may be repeated within a predetermined time interval, for example within five minutes, for up to a maximum predetermined number of times (e.g., four times maximum), after which the reminder can be automatically dismissed by the processing subsystem 22 if the user has not responded to any of the generated reminders. If an acceptance time window closes before the maximum number of Snooze reminders are generated, then the Snooze reminders may be automatically discontinued by the processing subsystem 22. If the Snooze reminder feature is incorporated in the device 10, then it is preferred that Snooze reminders for postprandial acceptance time windows be shorter than those presented for preprandial acceptance time windows. For example, postprandial Snooze reminders may occur every five minutes until the acceptance window is no longer available. Preprandial Snooze reminders may be spaced apart longer, for example every fifteen minutes, until a predetermined maximum number (e.g., four) such reminders have been presented. If the user accepts a given Snooze reminder but then does not enter a bG test value before the next Snooze reminder is scheduled to occur, then the next Snooze reminder may automatically be provided by the processing subsystem 22 as long as the current acceptance time window is open. If the currently open acceptance time window closes before the user has labeled a bG test value that matches the reminder for the acceptance window, then any remaining scheduled reminders are automatically cancelled by the processing subsystem 22.

If two acceptance time windows are open and overlapping one another, such as might be the case with a post-breakfast acceptance time window and a pre-lunch acceptance time window, and the user enters a bG test value which he/she has not marked with a specific label (i.e., either "Post-Breakfast" or "Pre-Lunch"), the processing subsystem 22 will prompt the user with a message on the display 16 to identify which one of the acceptance time windows the just-obtained bG test value is for. The user may then select on the touchscreen display 16, a label to be applied to the just-obtained bG test value from the displayed selection options.

It is also preferred that for the duration of a three day bG profile, the postprandial reminders should take precedence over any pre-existing postprandial reminders that the user has previously programmed in the device 10. After the three day bG profile has completed, any previously programmed postprandial bG time reminders may be reinstated by the processing subsystem 22. Also, if a three day bG profile is currently underway, the processing subsystem 22 preferably prevents the user from initiating another three day bG profile. If the user has initiated a three day bG profile and then one or two days later a scheduled subsequent three day bG test comes due to begin, the processing subsystem 22 may notify the user with a message on the display 16 that the current test is about to be terminated and the new, scheduled three day bG profile will be beginning. The software module 22a may include an option that enables the user to reschedule the scheduled three day bG test to a later date. The software module 22a also preferably notifies the user with a message on the touchscreen display 16 that when the 3 day bG profile has been successfully completed or has been terminated before completion.

The processing subsystem 22 and the software module 22a may also provide reminders to the user of user set upcoming medical visits, as well as prompts to conduct/schedule a three day bG profile before the user's next medical visit with a health care professional. The processing subsystem 22 may show a reminder on the display 16 to remind the user within, for example, two weeks of the next scheduled medical visit to conduct a three day bG profile. The processing subsystem 22 may clear the reminder if the user completes a three day bG profile prior to (e.g., three weeks prior to) the next scheduled medical visit. The software module 22a may also be configured with a default rescheduled test date if the user cancels a scheduled three day bG profile, which may, for example, occur on the next calendar day.

The software module 22a may also be configured to store at least one of a preprandial, postprandial, and bedtime bG target ranges specifically for use with the three day bG profile device 10. Such information may be used by the processing subsystem 22 and the software module 22a when showing (e.g., graphing) results of a three day bG profile on the display 16 after a test is completed. Stored default upper and lower limits for each target range may be modified by a user by selecting suitable options from the touchscreen display 16.

Also, a postprandial bG excursion of more than a default value, for example more than 50 mg/dL, may be stored and used by the processing subsystem 22 when analyzing the results of a three day bG profile. The software module 22a may also include a default hypoglycemic bG threshold value at or below which any bG value would be recognized as being hypoglycemic. In this instance the hypoglycemic bG value should be below the lower target of any of the bG target ranges.

Figure 3:
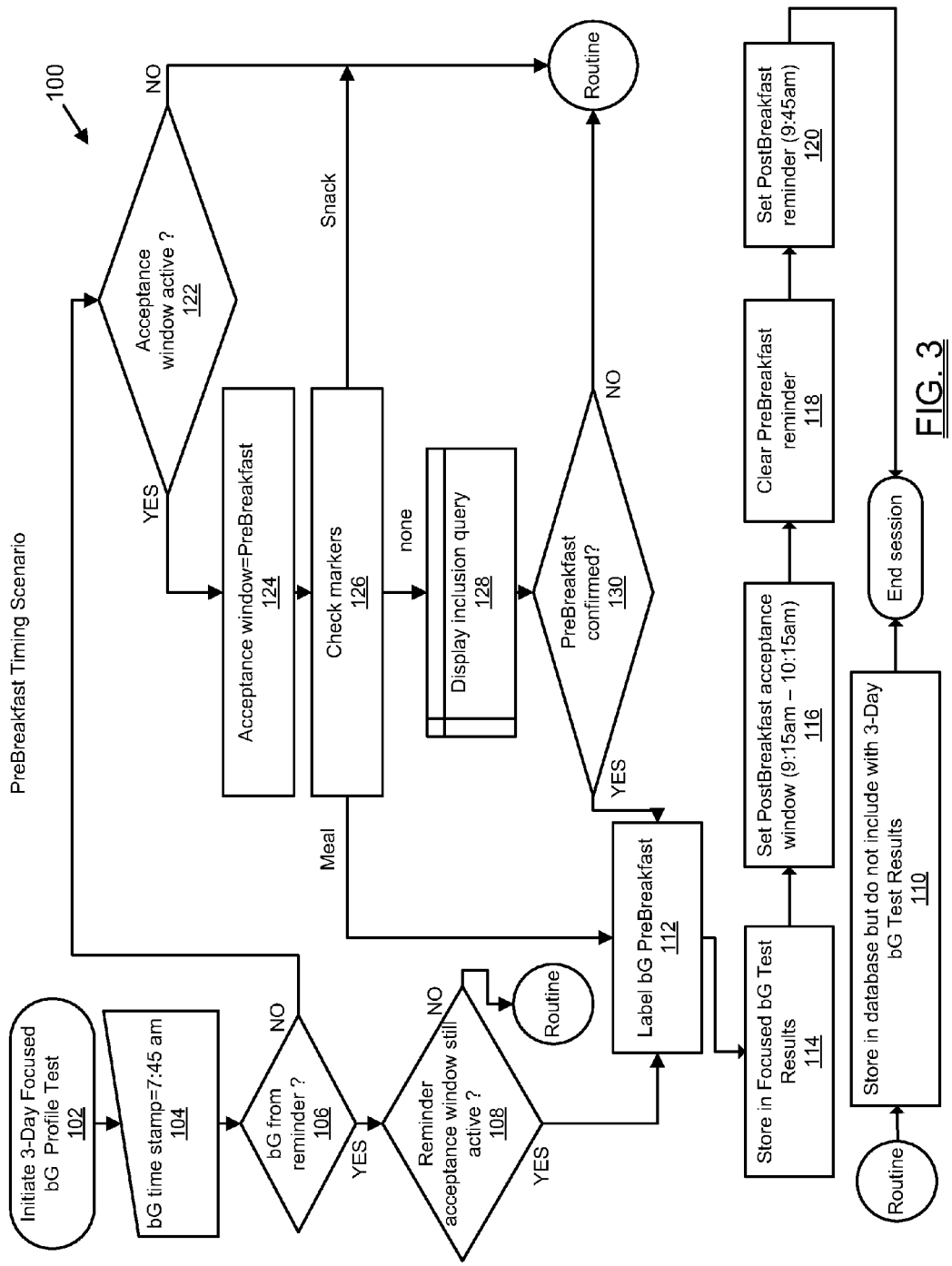
FIG. 3 is a flowchart illustrating an exemplary pre-breakfast (preprandial) timing scenario that may be performed in collecting bG test values pertaining to a pre-breakfast acceptance time window pursuant to obtaining a three day bG profile.

Referring now to FIG. 3, a high level flowchart 100 is shown that illustrates exemplary operations that may be implemented by the software module 22a as it runs on the processing subsystem 22. It will be appreciated that the flowchart of FIG. 3 is merely exemplary and that other operations could be included as well, besides those expressly shown, and that some operations shown in FIG. 3 may be omitted without departing from the general scope of operation described for FIG. 3. Also the order of operations of the flowchart 100 of FIG. 3, as well as the other flowcharts discussed herein, could potentially be altered while still achieving the same end result as that described herein.

At operation 102 a three day bG profile is initiated pursuant to a scheduled start date. At operation 104 the user obtains a bG test sample which is time stamped by the bG analyzer 24 with a time of 7:45 am. At operation 106 the processing subsystem 22 checks if the bG test value with the 7:45 am time stamp was generated in response to a pre-breakfast (i.e., preprandial) reminder. If so, then the processing subsystem 22 may optionally check to see if the reminder acceptance window is still active (i.e., open) at operation 108. If not, the processing subsystem 22 may store the bG test value in the database 26 (or memory 30), as indicated at operation 110, but will not include it in the three day bG profile results. If the answer to the inquiry at operation 108 is "Yes", then the bG test value may be accepted and labeled as a "Pre-breakfast" bG test value at operation 112, and stored in the database 26 (or memory 30) at operation 114 for inclusion in the three day bG profile results.

At operation 116 the Post-breakfast acceptance time window is set and at operation 118 the Pre-breakfast acceptance time window is cleared. The Post-breakfast time reminder is set to be provided at a predetermined time (in this example 9:45 am), as indicated at operation 120, in relation to the user input typical breakfast time.

If the inquiry at operation 106 indicates that a bG test value was not provided pursuant to a reminder then a check is made if any acceptance time window is still active (i.e., open), as indicated at operation 122. If not, then the just-obtained bG test value may be stored in the database 26 (or memory 30), as indicated at operation 110, but will not be included as part of the three day bG profile results. If the inquiry at operation 122 indicates that the current acceptance time window is still open, then at operation 124 the processing subsystem 22 confirms that the Pre-breakfast acceptance time window is still open and then checks to see if the user has entered a marker for the just-obtained bG test value, as indicated at operation 126. If the check at operation 126 indicates that a bG test value has been entered by the user with a marker identifying it as a "meal", then operations 112-120 are repeated. If the check at operation 126 reveals that a marker has been entered by the user for a snack, then operation 110 is repeated so that the bG test value is stored in the database 26 but not used in the results that form the 3 day bG profile. If the check at operation 126 reveals that a bG test value has been entered by the user but without a label, then the processing subsystem 22 displays a query in the display 16 prompting the user to select whether the bG test value entered is a preprandial or postprandial bG test value, as indicated at operation 128. If the bG test value turns out to be a Pre-breakfast bG test value (i.e., preprandial bG value), as determined at operation 130, then operations 112-120 are carried out. If the check at operation 130 indicates that the bG was not labeled as Pre-Breakfast, then operation 110 is carried out to store the bG test value, but it will not be included in the three day bG profile results. It will be appreciated that for simplicity, the instance of having two or more overlapping acceptance time windows has not been included in the example of FIG. 3.

Figure 4:
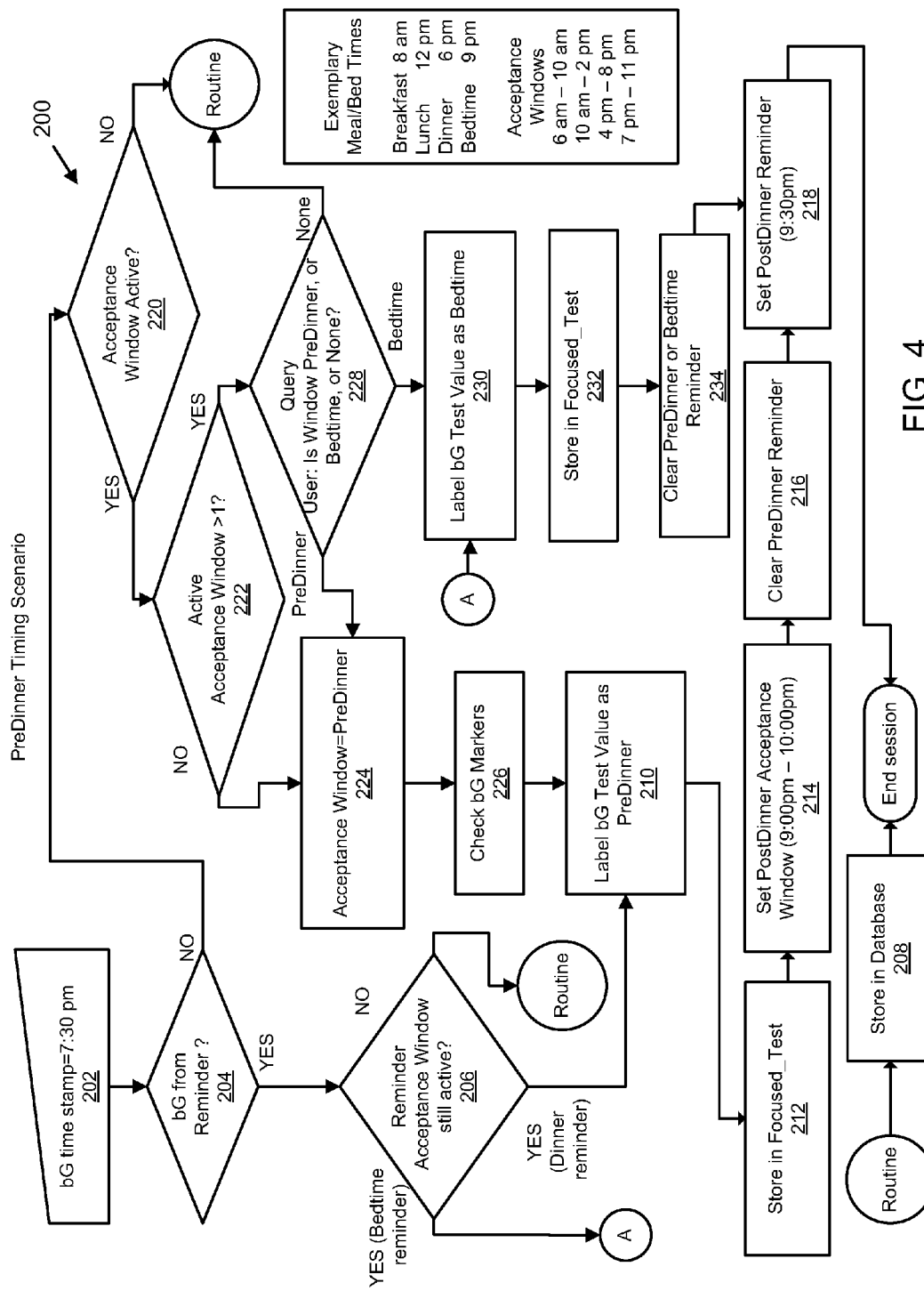
FIG. 4 is a flowchart illustrating an exemplary pre-dinner timing scenario that may be performed in collecting bG test values pertaining to a pre-dinner acceptance time window, pursuant to obtaining a three day bG profile.

Referring to FIG. 4, a flowchart 200 is shown of an exemplary Pre-dinner timing scenario that may be implemented using the device 10. Again, flowchart 200 represents a high level flowchart and additional operations could easily be incorporated as desired, while potentially one or more operations could be eliminated or merged with other operations. The order of operations could also potentially be changed while still achieving the same result as that described before for FIG. 4.

At operation 202 the user provides a bG test sample having a time stamp of 7:30 pm. At operation 204 a check is made to determine if the bG test value has been entered pursuant to a reminder. If so, then at operation 206 a check is made to see if the reminder acceptance window is still open and what type of reminder was given. If no reminder window is still open, then the bG test value may be stored in the relational database 26 at operation 208 but will not be used as part of the test results for the three day bG profile. If the check at operation 206 indicates that the reminder acceptance window for a Pre-dinner reminder is still active, then the bG test value may be automatically labeled as a "Pre-dinner" bG test value at operation 210 and stored in the database 26 at operation 212 as part of the three day bG profile results. If the check at operation 206 reveals that the reminder was associated with a "Bedtime" event, then operations 230-234 may be performed to automatically label the bG test value as a "Bedtime" bG test value, then store the bG test value in the relational database 26, and then clear the previously given reminder. By "reminder acceptance window" it is meant a short time interval, for example five minutes, after a reminder is generated.

At operation 214 the Post-dinner acceptance time window is set. At operation 216 the Pre-dinner reminder is cleared and at operation 218 the Post-dinner reminder is then set to provide the first Post-dinner reminder at 9:30 pm.

Operations 204 and 206, described above, may be optional. But if they are included it means that when the processing subsystem 22 detects that the bG test value is entered within a specific number of minutes of the Pre-dinner reminder being given (e.g., five minutes), then the processing subsystem 22 will simply recognize the bG test value as a Pre-dinner bG test value. This logic will require that the processing subsystem 22 set an additional reminder timer acceptance window when the Pre-dinner acceptance time window is opened, with the additional reminder timer acceptance window being a much shorter duration timer than the timer that is used for the Pre-dinner acceptance time window.

Returning to the flowchart 200 of FIG. 4, if the check at operation 204 indicates that the bG test value was not made during a reminder acceptance window, then a check is made to see if the Pre-dinner acceptance time window is still active, as indicated at operation 220. If not, then the bG test value may be stored at operation 208 but will not be used as part of the test results that form the three day bG profile.

If the check at operation 220 indicates that the Pre-dinner acceptance time window is still active, then a check is made at operation 222 to determine if more than one acceptance time window is currently active. If not, then the processing subsystem 22 determines that the Pre-dinner acceptance time window is the only window currently still active, as indicated at operation 224. A check is then made to determine what label, if any, has been applied by the user to the just-obtained bG test value, as indicated at operation 226. Operation 226 may essentially be the same framework of checks as described above for operations 126, 128 and 130 of FIG. 3. Assuming that operation 226 identifies the bG test value as having a preprandial marker, then operations 210-218 are repeated. If operation 222 indicates that more than one acceptance time window is currently open, then the processing subsystem 22 generates a query on the display 16 at operation 228 requesting the user to identify if the bG test value is a Pre-dinner or bedtime bG test value. This may be a pair of radio selection boxes labeled "Pre-dinner" and "Bedtime" that the user may select using the touchscreen display 16. If the user marks the bG test value as a Pre-dinner bG test value, then operations 224, 226 and 210-218 are repeated. If the user indicates the bG test value is associated with a Bedtime, then the processing subsystem 22 labels the bG test value as a "Bedtime" bG test value, as indicated at operation 230, and then stores it in the database 26, as indicated at operation 232. The Bedtime reminder is then cleared at operation 234.

Figure 5:
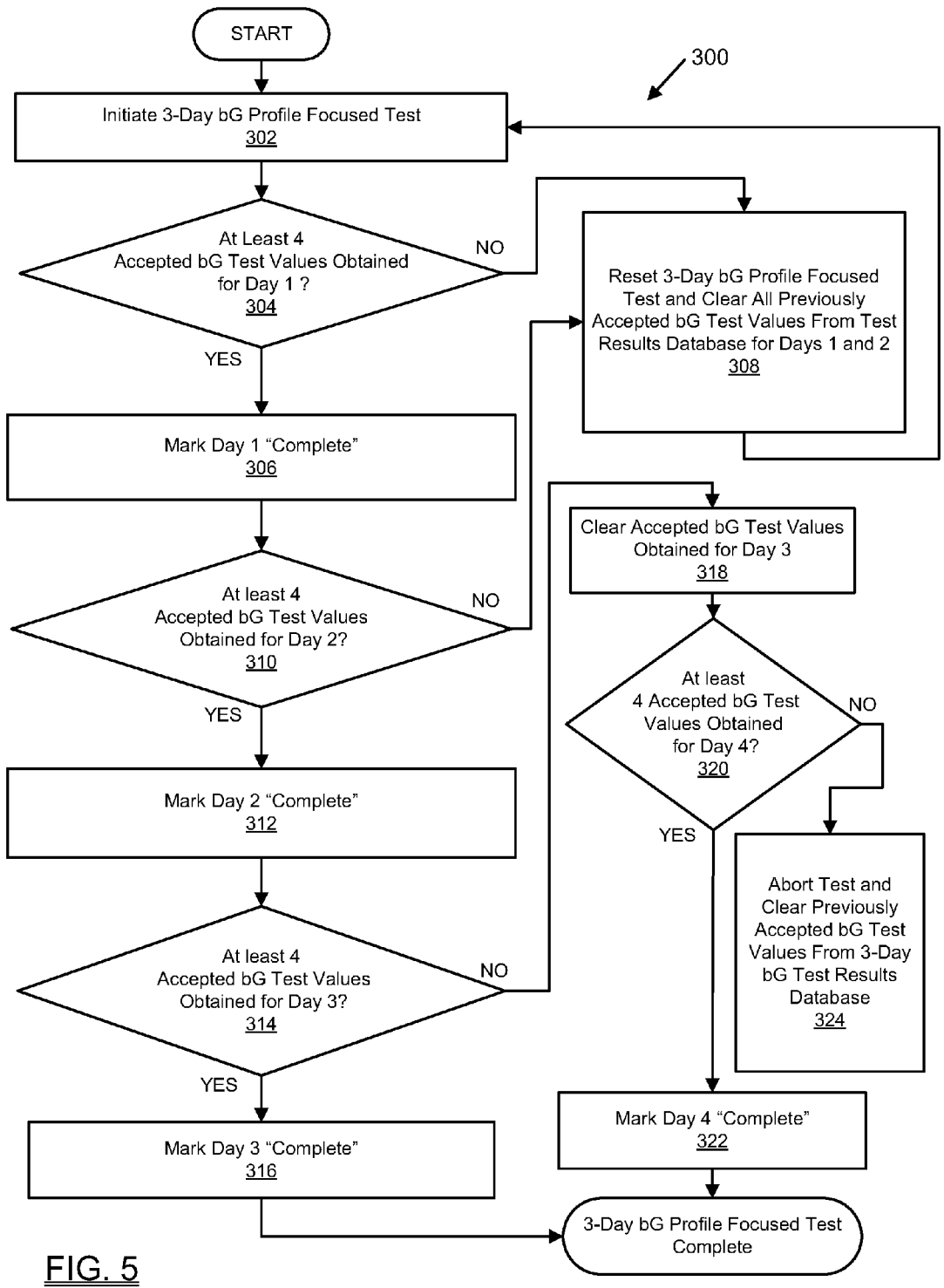
FIG. 5 is a flowchart illustrating exemplary operations that may be implemented by the device in collecting bG test values from a user during a three day bG profile period.

Referring now to FIG. 5, an exemplary high level flowchart 300 is shown that sets forth various operations that may be taken by the processing subsystem 22 in managing the three day bG profile. By "managing" it is meant checking the accumulated bG test values stored in the database 26 at the end of each day to ensure that sufficient bG test samples have been accepted to warrant continuing with the test, clearing previously accepted bG test values if an adequate number of bG values is not obtained on a given day, and potentially restarting the test if needed. At operation 302 the three day bG profile is initiated. At the end of day one the processing subsystem 22 checks to determine if at least four bG test values have been accepted during the preceding twenty four hour period, as indicated at operation 304. If so, then the day one bG test results in the relational database is marked "Complete", as indicated at operation 306. If the check at operation 304 reveals that less than four accepted bG test values were obtained during day one, then the processing subsystem 22 may automatically reset the three day bG profile and clear the previously stored, accepted bG test values from the collection of results being used for the test, as indicated at operation 308. It will be appreciated, however, that the recorded bG test values are not completely erased from the database 26 but rather only that they are deleted from within the database 26 where test results are compiled for the three day bG profile. The three day bG profile is then restarted at operation 302. The processing subsystem 22 preferably provides messages on the touchscreen display 16 that the present test has been cancelled and that a new test is being initiated.

If at least four accepted bG test values are obtained on day one, as indicated at operation 304, then a check is made at the end of day two to determine if at least four accepted bG test values were obtained during the twenty four hour period comprising day two, as indicated at operation 310. If the check at operation 310 indicates that at least four accepted bG test values were recorded during day two, then the database entries for the accepted day two bG test values is marked "Complete" by the processing subsystem 22, as indicated at operation 312. If the check at operation 310 indicates that fewer than four accepted bG test values were recorded during the twenty four hour period for day two, then operation 308 is repeated to clear all of the previously accepted bG test values recorded for days one and two, and the currently underway test is aborted and restarted at operation 302. Again, the bG test values recorded in the database 26 for days one and two are not completely erased from the database 26, but rather only erased from the specific file (or files) that are holding bG test values for use in the three day bG profile.

If at least four accepted bG test values are obtained during day two, then the accepted day two bG test values are marked "Complete" (operation 312), and the processing subsystem 22 will check at the end of the next day (i.e., day three) to see if at least four accepted bG test values have been recorded, as indicated at operation 314. If so, then the day three recorded bG test values in the database 26 are marked "Complete", as indicated at operation 316, and the three day bG profile is concluded. A message informing the user of the successful completion of the test may be displayed on the touchscreen display 16. If the check at operation 314 indicates that fewer than four accepted bG test values were obtained during the twenty four hour period comprising day three, then at operation 318 the processing subsystem 22 clears the previously recorded, accepted bG test values obtained for day three only from the database 26 where these values are being recorded for the three day bG profile. The processing subsystem 22 then continues carrying out the three day bG profile during the subsequent day (i.e., day four), as indicated at operation 320. At the end of day four a check is made to determine if at least four accepted bG test samples have been obtained, as indicated at operation 320. If so, then the day four database entries are marked "Complete", as indicated at operation 322, and the three day bG profile is concluded. If the check at operation 320 indicates that fewer than four accepted bG test samples were obtained during the twenty four hour period comprising day four, then all of the previously accepted bG test samples are cleared from the database 26 where the three day bG profile results have been recorded, and the test is aborted, as indicated at operation 324. A message informing the user of this action may be provided on the touchscreen display 16 along with an option for the user to restart the test on the following day or to reschedule the test for a later date. Again, the stored bG values are not deleted entirely from the database 26, but only from the test results recorded for purposes of collecting test data for the three day bG profile.

It will be appreciated that the results of a given three day bG profile may be stored indefinitely in the device 10, or stored for a fixed number of three day profile tests, or stored for a predetermined time period before being automatically erased by the processing subsystem 22. The test results may be presented in a graphical format along with the predefined bG target ranges. If the touchscreen display 22 is a color touchscreen display, this enables various colors to be used to highlight the bG target ranges. Any bG excursions for a given one of the accepted bG test values plotted on a graph may also be identified with a different color. The interface 28 (FIG. 1) enables the stored test results to be downloaded by a health care professional onto a different medium (e.g., laptop or desktop computer) for use by the professional and/or made a part of a permanent electronic health record for the user.

In one aspect the present disclosure relates to a method for managing three day profile blood glucose (bG) measurements provided by a user on a handheld diabetes management device. The method can comprise configuring a database of the device to store a plurality of bG test values input by a user for each day of a three day test period, wherein bG test values are required to be provided by the user in accordance with a predetermined plurality of differing acceptance time windows during each day of the three day test period. A processing subsystem of the device can be used to receive bG test values provided by the user and to store the bG test values in the database of the device. The method allows two acceptance time windows to be opened at the same time, and if a given bG test value is obtained during such a condition, then the user is allowed to select which one of the open acceptance time windows to associate the given bG test value with. The processing subsystem can be used to determine if at least a predetermined minimum plurality of the stored bG test values has been provided by the user during the predetermined plurality of differing acceptance time windows for each day of the three day test period. If so, the processing subsystem can accept the bG test values for the purpose of compiling results for a three day bG profile. The method can further comprise using a display of the device to display the results of the three day bG profile. Furthermore, the three day test period during which the bG test values are provided to the processing subsystem can require at least the predetermined minimum plurality of the bG test values to have been provided by the user during the predetermined plurality of differing acceptance time windows during both of first and second successive days that form the three day test period. Still further, the processing subsystem can be configured to abort a collection of the bG test values and restart the three day test period if at least the predetermined minimum plurality of bG test values is not provided during a first day of the three day test period. Still further, the processing subsystem can remove a collection of the bG test values, from a file of the database, that were obtained during the first and second days of the three day test period, if the predetermined minimum plurality of bG test values is provided during a first day of the three day test period but not during the second day of the three day test period. Moreover, the predetermined plurality of differing time acceptance windows can comprise seven different acceptance time windows each having a predetermined duration. Furthermore, the seven different acceptance time windows can comprise: a pre-breakfast meal acceptance time window with a user selected breakfast time input to the processing subsystem by the user; a post-breakfast meal acceptance time window; a pre-lunch meal acceptance time window; with a user selected lunch time input to the processing subsystem by the user; a post-lunch meal acceptance time window; a pre-dinner meal acceptance time window with a user selected dinner time input to the processing subsystem by the user; a post-dinner meal time acceptance window; and a pre-bedtime meal acceptance time window with a user selected bed time input to the processing subsystem. Furthermore, the processing subsystem can be used to cause the device to generate one of a tactile and audible reminder, at each one of the predetermined plurality of differing acceptance time windows, to alert the user to conduct a bG test in accordance with a specific one of the acceptance time windows. Still further, the processing subsystem can be used to receive information from the user designating a bG test value being input to the device, wherein the bG test value relates to a snack or a meal, and wherein the device only uses bG test values that correspond to a meal. Moreover, the processing subsystem can recognize that at least two of the predetermined plurality of differing acceptance time windows overlap relative to a user set meal time, and the processing system can prompt the device to query the user to define whether a given bG test value input by the user corresponds is a preprandial bG test value or a postprandial test value, and the processing subsystem can generate a plurality of selection choices on a display of the device that allows the user to specify whether the given bG test value is a preprandial bG test value or a postprandial bG test value. Still further, the display can be implemented as a touchscreen display, and the selection choices can comprise choices that are presented on the touchscreen for selection by the user.

In another aspect the present disclosure relates to a non-transitory, computer readable medium. The computer readable medium is adapted to run on a processing subsystem of a handheld diabetes device for managing three day profile blood glucose (bG) measurements input by a user to the device. The computer readable medium can comprise a database that stores a plurality of bG test values input to the device by a user for each day of a three day test period. The bG test values can be provided by the user in accordance with a predetermined plurality of differing acceptance time windows during each day of the three day test period. The computer readable medium is adapted to determine if at least a predetermined minimum plurality of the stored bG test values has been accepted during the predetermined plurality of differing acceptance time windows for each day of the three day test period. If so, the accepted bG test values are used as test results for a three day bG profile. The computer readable medium is also able to determine if the first two days of the three day test period each have the minimum plurality of the stored bG test values obtained therefore, and that the third day does not, and then enables the test to continue on a successive fourth day following the third day in an attempt to successfully complete the three day test period. The test results are sent to a display of the device for display to the user. The non-transitory, computer readable medium can be adapted to determine if the bG test values input to the device by the user have been provided during the predetermined plurality of differing acceptance time windows during both of first and second successive days that form the three day test period. Still further, the predetermined plurality of differing acceptance time windows can be implemented in accordance with seven different acceptance time windows over a twenty four hour period, with each one of the seven different acceptance time windows having a predetermined time duration. The processing subsystem can also be used to analyze a marker for each of the bG test values that is provided by the user, and further can allow only specific ones of those bG test values to be used for the three day profile that: have been marked by the user as corresponding to a meal; and that have been input by the user during ones of the predetermined plurality of differing acceptance time windows.

In another aspect the present disclosure relates to a system for managing three day profile blood glucose (bG) measurements provided by a user. The system can comprise a handheld diabetes management device. The device can include a database for storing bG values input to the device by a user for each day of a three day test period. The device can also include a processing subsystem in communication with the database. The processing system can be configured to perform several operations: to generate a plurality of acceptance time windows for a twenty four hour period; to analyze the bG test values stored in the database during each twenty four hour period for each day over a three day period; to determine whether each of the stored bG test values corresponds to a meal; to accept only ones of the bG test values input by the user that correspond to a meal, and that have been input during specific ones of the plurality of acceptance time windows over the three day period; and to use the accepted bG values in generating information relating to test results for a three day bG profile. The system can also determine if a sufficient number of accepted bG test values has been obtained for each of the first and second days of the three day test, but the third day of the test did not, then allowing the user to attempt to complete the test by entering bG test values on a fourth day following the third day of the test. The handheld diabetes management device may further include a display that displays the results of the three day bG profile. The processing subsystem can further be configured to abort the three day test period, and to start a new three day test period, if: at the end of the first day of the three day time test period at least four accepted bG test values have not obtained for the first day; or at the end of the second day of the three day test period at least four accepted bG test values have not been obtained for the second day. If at least four accepted bG test values are obtained during each of the first and second days, and only three or fewer accepted ones of the bG test values are obtained during the third day, the processing subsystem can also be configured to clear the previously accepted bG test values obtained during the third day from a collection of the test results, and to enable bG test values to be input to the device by the user during the fourth day immediately following the third day, and if at least four accepted bG test values are obtained during the fourth day, then the processing subsystem can use the accepted bG test values obtained during the first, second and fourth days to form the three day bG profile results. The predetermined acceptance time windows are implemented by the processing subsystem as seven acceptance time windows throughout a twenty four hour period, and wherein six of the seven acceptance time windows are set in relation to specific meal times input to the device by the user, and a seventh time window is set in relation to a bed time input to the device by the user.

It will be appreciated that while various embodiments have been described, those skilled in the art will recognize modifications or variations which might be made without departing from the present disclosure. Thus, the present examples are not intended to limit the present disclosure. Therefore, the description and claims should be interpreted liberally with only such limitation as is necessary in view of the pertinent prior art.

What is claimed is:

1. A method for managing three day profile blood glucose (bG) measurements provided by a user on a handheld diabetes management device, the method comprising:
   configuring a database of the device to store a plurality of bG test values input by a user for each day of a three day test period, wherein bG test values are required to be provided by the user in accordance with a predetermined plurality of differing acceptance time windows during each day of the three day test period;
   receiving, by a processing subsystem of the device, a given bG test value at a given time;
   recognizing, by the processing subsystem, that at least two of the predetermined plurality of differing acceptance time windows overlap relative to a user set meal time;
   prompting, by the processing subsystem, user to select an acceptance time window from the at least two acceptance time windows proximate to the given time when the at least two acceptance time windows are open concurrently;
   receiving, by the processing subsystem, a selected acceptance time window from the at least two acceptance time windows, associating the given bG test value with the selected acceptance time window and storing the given bG test value in the selected acceptance time window;
   determining, by the processing subsystem, whether a predetermined minimum plurality of the stored bG test values has been provided by the user during the predetermined plurality of differing acceptance time windows for a given day of the three day test period and accepting the bG test values provided by the user as three day bG profile results when the predetermined minimum plurality of the stored bG test values has been provided by the user for the given day; and
   discarding the bG test values when the predetermined minimum plurality of bG test values is not provided for the given day of the three day test period.

2. The method of claim 1, further comprising using a display of the device to display the results of the three day bG profile.

3. The method of claim 1, wherein the three day test period during which the bG test values are provided to the processing subsystem requires at least the predetermined minimum plurality of the bG test values to have been provided by the user during the predetermined plurality of differing acceptance time windows during both of first and second successive days that form the three day test period.

4. The method of claim 1, wherein the processing subsystem is configured to restart the three day test period when the predetermined minimum plurality of bG test values is not provided during any one day of the three day test period.

5. The method of claim 1, wherein the processing subsystem removes a collection of the bG test values, from a file of the database, that were obtained during the first and second days of the three day test period, when the predetermined minimum plurality of bG test values is provided during a first day of the three day test period but not during the second day of the three day test period.

6. The method of claim 1, wherein the predetermined plurality of differing time acceptance windows comprises seven different acceptance time windows each having a predetermined duration.

7. The method of claim 6, wherein the seven different acceptance time windows comprise:
   a pre-breakfast meal acceptance time window with a user selected breakfast time input to the processing subsystem by the user;
   a post-breakfast meal acceptance time window;
   a pre-lunch meal acceptance time window; with a user selected lunch time input to the processing subsystem by the user;
   a post-lunch meal acceptance time window;
   a pre-dinner meal acceptance time window with a user selected dinner time input to the processing subsystem by the user;
   a post-dinner meal time acceptance window; and
   a bedtime meal acceptance time window with a user selected bedtime input to the processing subsystem.

8. The method of claim 1, wherein the processing subsystem is used to cause the device to generate one of a tactile land audible reminder, at each one of the predetermined plurality of differing acceptance time windows, to alert the user to conduct a bG test in accordance with a specific one of the acceptance time windows.

9. The method of claim 1, wherein the processing subsystem only considers postprandial labeled bG test values that meet a user preset snack threshold level indicating that a particular bG test value was obtained subsequent to a meal and not subsequent to a snack.

10. The method of claim 1, wherein the display is implemented as a touchscreen display, and wherein the selection choices comprise choices that are presented on the touchscreen for selection by the user.

11. A non-transitory, computer readable medium adapted to run on a processing subsystem of a handheld diabetes management device for managing three day profile blood glucose (bG) measurements input by a user to the device, the computer readable medium comprising:
   a database that stores a plurality of bG test values input to the device by a user for each day of a three day test period, wherein bG test values are required to be provided by the user in accordance with a predetermined plurality of differing acceptance time windows during each day of the three day test period; and the computer readable medium adapted to determine whether a predetermined minimum plurality of the stored bG test values has been accepted during the predetermined plurality of differing acceptance time windows for each day of the three day test period and using the accepted bG test values as test results for a three day bG profile when the predetermined minimum plurality of the stored bG test values has been accepted during the predetermined plurality of differing acceptance time windows for each day of the three day test period; and the computer readable medium adapted to determine whether the first two days of the three day test period each have the minimum plurality of the stored bG test values obtained therefore and that the third day does not, and clear the previously accepted bG test values obtained during the third day from the database when the first two days of the three day period each have the minimum plurality of the stored bG test values obtained therefore and that the third day does not; and enabling the test to continue on a successive fourth day following the third day in an attempt to successfully complete the three day test period when the first two days of the three day test period each have the minimum plurality of the stored bG test values obtained therefore and the third day does not, and using the accepted bG test values obtained during the first, second and fourth days to form the three day bG profile results.

12. The non-transitory, computer readable medium of claim 11, wherein the test results are sent to a display of the device for the display to the user.

13. The non-transitory, computer readable medium of claim 11, wherein the non-transitory, computer readable medium is adapted to determine whether the bG test values input to the device by the user have been provided during the predetermined plurality of differing acceptance time windows during both of first and second successive days that form the three day test period.

14. The non-transitory, computer readable medium of claim 11, wherein the predetermined plurality of differing acceptance time windows are implemented in accordance with seven different acceptance time windows over a twenty four hour period, with each one of said seven different acceptance time windows having a predetermined time duration.

15. The non-transitory, computer readable medium of claim 11, wherein the non-transitory, computer readable medium uses the processing subsystem to analyze a marker for each of the bG test values that is provided by the user, and further allows only specific ones of those bG test values to be used for the three day profile that:

have been marked by the user as corresponding to a meal; and that have been input by the user during ones of the predetermined plurality of differing acceptance time windows.

16. A system for managing three day profile blood glucose (bG) measurements provided by a user, the system comprising:

a handheld diabetes management device, the device including;

a database for storing bG values input to the device by a user for each day of a three day test period;

a processing subsystem in communication with the database, the processing subsystem configured:

to generate a plurality of acceptance time windows for a twenty four hour period;

to analyze the bG test values stored in the database during each twenty four hour period for each day of a three day test period;

to determine whether each of other stored bG test values corresponds to a meal;

to accept only ones of the bG test values input by the user that correspond to a meal, and that have been input during specific ones of the plurality of acceptance time windows over the three day time span;

to allow the user to continue performing the test on a fourth day when the first and second days of the test result in a sufficient number of bG test values being accepted but the third day has an insufficient number of accepted bG test values, in an effort to successfully complete the test;

to clear the previously accepted bG test values obtained during the third day from the database when the first and second days of the test result in a sufficient number of bG test values being accepted but the third day has an insufficient number of accepted bG test values;

to use the accepted bG values in generating information relating to test results for a three day bG profile; and the handheld diabetes management device further including a visual display for displaying the test results of the three day bG profile.

17. The system of claim 16, wherein the processing subsystem is further configured to abort the three day test period, and to start a new three day test period, when if:

at the end of the first day of the three day time test period at least four accepted bG test values have not obtained for the first day; or at the end of the second day of the three day test period at least four accepted bG test values have not been obtained for the second day.

18. The system of claim 16, wherein the predetermined acceptance time windows are implemented by the processing subsystem as seven acceptance time windows throughout a twenty four hour period, and wherein six of the seven acceptance time windows are set in relation to specific meal times input to the device by the user, and a seventh time window is set in relation to a bed time input to the device by the user.

* * * * *

UNITED STATES PATENT AND TRADEMARK OFFICE
CERTIFICATE OF CORRECTION

| | | |
|---|---|---|
| PATENT NO. | : 8,515,775 B2 | Page 1 of 1 |
| APPLICATION NO. | : 12/905417 | |
| DATED | : August 20, 2013 | |
| INVENTOR(S) | : Galley et al. | |

It is certified that error appears in the above-identified patent and that said Letters Patent is hereby corrected as shown below:

In the Specification:

Column 5, line 5, delete "user control switches" and insert --unit control switches--.

Column 5, line 24, delete "24a" and insert --24--.

Column 5, line 30, delete "user control panel" and insert --unit control switches--.

In the Claims:

Column 16, line 33 (claim 7), delete "user:" and insert --user;--.

Column 16, line 35 (claim 7), delete "window;" and insert --window--.

Column 16, line 47 (claim 8), delete "land" and insert --and--.

Signed and Sealed this
Third Day of June, 2014

Michelle K. Lee
*Deputy Director of the United States Patent and Trademark Office*